United States Patent [19]

Furutani et al.

[11] Patent Number: 5,612,192
[45] Date of Patent: Mar. 18, 1997

[54] DNA BASE SEQUENCE CONTAINING REGIONS INVOLVED IN THE PRODUCTION AND SECRETION OF A PROTEIN, RECOMBINANT DNA INCLUDING THE WHOLE OR A PART OF THE DNA BASE SEQUENCE, AND METHOD OF PRODUCING PROTEINS BY USE OF THE RECOMBINANT DNA

[75] Inventors: Yoshio Furutani, Miuragun; Hiroaki Shimada, Mobara; Izumi Mita, Mobara; Kazuaki Manabe, Mobara; Masaru Honjo, Mobara; Noboru Tomioka, Mobara, all of Japan

[73] Assignees: Agency of Industrial Science and Technology; Extra-Ministerial Bureau of Ministry of International Trade and Industry, both of Tokyo, Japan

[21] Appl. No.: 359,863

[22] Filed: Dec. 20, 1994

Related U.S. Application Data

[63] Continuation of Ser. No. 988,015, Dec. 9, 1992, abandoned, which is a continuation of Ser. No. 628,989, Dec. 17, 1990, abandoned, which is a continuation of Ser. No. 159,513, Feb. 19, 1988, abandoned, which is a continuation of Ser. No. 686,892, Dec. 27, 1984, abandoned.

[30] Foreign Application Priority Data

Dec. 28, 1983 [JP] Japan .................................. 58-245065
Apr. 3, 1984 [JP] Japan .................................. 59-65156
Aug. 24, 1984 [JP] Japan .................................. 59-175158

[51] Int. Cl.$^6$ ............................ C12N 15/00; C12P 21/00
[52] U.S. Cl. ................ 435/69.1; 435/252.3; 435/252.31; 435/320.1
[58] Field of Search .................................. 435/69.1, 71.2, 435/172.3, 252.3–252.35, 832–839, 2, 9, 221, 320.1, 91.1; 935/14, 29, 38, 41, 45, 47.51, 72, 74; 536/23.2, 23.7, 24.1

[56] References Cited

U.S. PATENT DOCUMENTS 4,801,537 1/1989 Nagarajan et al. ........................ 435/68
5,015,574 5/1991 Furutani et al. ........................ 435/67.1

FOREIGN PATENT DOCUMENTS 0114695  8/1984  European Pat. Off. .
16229183 9/1983  Japan .
59-19084 4/1984  Japan .
8404541  11/1984 WIPO .

OTHER PUBLICATIONS

Shimada, H., et al, (1985), J. Biotechnol., 2:75–85.
D.J. Henner, et al., "Upstream Activating Sequences In Bacillus Subtilis", in *Genetics and Biotechnology of Bacilli*, 1988, Ganesan et al (ed.), pp. 3–9.
M. Perego et al., (1988), J. Bacteriol., 170(6):2560–2567.
D.J. Henner et al., (1988), J. Bacteriol., 170(1):296–300.
Bacillus Genetic Stock center, Strains & Data, Fourth Edition, (1989), pp. 2.1, 2.2 and 2.12.
M. Honjo et al., (1984), J. Biotechnol., 1:265–277.
Yang, et al. "Identification of the Pleiotropic sacQ Gene of *Bacillus subtilis*." J. Bacteriol., vol. 166, No. 1 (Apr. 1986), 113–119.
Tomioka et al. "Cloning, sequencing, and some properties of a novel *Bacillus amyloliquefaciens* gene involved in the increase of extracellular protease activities." *Journal of Biotechnology*, 3, (1985), 85–96.
Chang et al. "High Frequency Transformation of *Bacillus subtillis* Protoplasts by Plasmid DNA." *Molec. gen. Genet.*, 168, (1979), 111–115.
Marmur, J. "A Procedure for the Isolation of Deoxyribonucleic Acid from Micro–organisms." *J. Mol. Biol.*, 3, (1961), 208–218.
Maxam et al. "A new method for sequencing DNA." *Proc. Natl. Acad. Sci. USA*, vol. 74, No. 2, (Feb. 1977), 560–564.
Birnboim et al. "A rapid alkaline extraction procedure for screening recombinant plasmid DNA." *Nucleic Acids Research*, vol. 7, No. 6, (1979), 1513–1523.
Hagihara et al. "Crystalline Bacterial Proteinase." *The Journal of Biochemistry*, vol. 45, No. 3, (1958), 185–194.
Chang et al. "Cloning and expression of heterologous genes in *Bacillus subtilis*." (NSC Symp. Ser, 4, (1982), 254–62) *Chemical Abstracts* 100:46295m.
Blobel et al. "Transfer of Proteins Across Membranes." *The Journal of Cell Biology*, 67, (1975), 835–851.
Gryczan et al. "Characterization of *Staphylococcus aureus* Plasmids Introduced by Transformation into *Bacillus subtilis*." *J. Bacteriol.*, vol. 134, No. 1, Apr. 1978), 318–329.
Yamaguchi et al. "Isolation of Mutants Defective in α–Amylase from *Bacillus subtilis*: Genetic Analyses." *J. Bacteriol.*, vol. 119, No. 2, (Aug. 1974), 416–424.
Eiji Ishikawa et al., eds., *Enzyme Immunoassay*, (Tokyo: Igaku–Shoin Ltd., 1981), pp. 67–80.
Saito et al. "Preparation of Transforming Deoxyribonucleic Acid by Phenol Treatment." *Biochem. Biophy. Acta*, 72 (1963), 619–629.
Takeichi et al. "Cloning of *Bacillus subtilis* α–Amylase Structural Gene in Plasmid pUB110." *Agric. Biol. Chem.*, vol. 47, No. 1, (1983), 159–161.

(List continued on next page.)

*Primary Examiner*—James Martinell
*Attorney, Agent, or Firm*—Fisher, Christen & Sabol

[57] ABSTRACT

A neutral protease gene of *Bacillus amyloliquefaciens* is cloned, which gene comprises the promoter region, the ribosome binding region, the region involved in the secretion of the neutral protease, the region consisting of the structural gene for the neutral protease, and the terminator region. Each of the regions is useful as a material for construction of a recombinant DNA used for the production of proteins by culturing a host bacterium transformed with the recombinant DNA. For example, the extracellular production of neutral protease in a large amount can be accomplished by culturing *B. subtilis* transformed with a recombinant DNA comprising pUB110 and the neutral protease gene.

13 Claims, 4 Drawing Sheets

OTHER PUBLICATIONS

Mandel et al. "Calcium–dependent Bacteriophage DNA Infection." *J. Mol. Biol.*, 53, (1970), 159–162.

Uehara et al. "Regulation of Neutral Protease Productivity in *Bacillus subtilis:* Transformation of High Protease Productivity." *J. Bacteriol.*, 119, (1974), 82–91.

Hidetsngu Fuwa "A New Method for Microdetermination of Amylase Activity By The Use of Amylose As The Substrate." *The Journal of Biochemistry*, vol. 41, No. 1, (1954), 583–603.

Takegi et al. "Nucleotide Sequence and Promoter Region for the Neutral Protease Gene from *Bacillus stearothermophilus*", vol. 163, No. 3, (Sep. 1985), 824–831.

I.R. Lehman, "T4 DNA Polymerase" *Method in Enzymology*, vol. 29, (1978), 46–57. Biochemical Information II, Boehringer Mannheim, pp. 28–30.

Patents Abstracts of Japan 7(285).

Patents Abstracts of Japan, 8(156).

Levy et al; Chem. Abstr. 84:27437u (1976).

Moran, Jr., et al., Mol. Gen. Genet., 186, 339 (1982).

Debabov, "The Molecular Biology of the Bacilli", 1, 331–333 (1982), Dubnau, D.A. ed., Acedemic Press.

Goldfarb, D.S., et al., Nature, 293, 309 (1981).

Williams, D.M., et al., Gene, 16, 199 (1981).

Palva, et al., Gene, 15, 43 (1981).

Otsuka et al, "Chemical synthesis of DNA", Kagaku no Ryoiki (Field of Chemistry), vol. 10, No. 35, (1981), p. 762 (lines 1–24).

Anagnastopoulos et al; J. Bacteriol. 81: 741 (1961).

Fujii et al, "Molecular cloning of a thermostable neutral protease gene from *Bacillus stearothermophilus* in a vector plasmid and its expression in *Bacillus stearothermophilus* and *Bacillus subtilis*", J. Bacteriol. 154: 831 (1983).

Honjo et al, "Cloning and expression of the gene for neutral protease of *Bacillus amyloliquefaciens* in *Bacillus subtilis*", Chem. Abstr. 103 :82709v (1985) of J. Biotechnol. 1: 265 (1984).

Vasantha et al, "Genes for alkaline protease and neutral protease from *Bacillus amyloliquefaciens* conatin a large open reading frame between the regions coding for signal sequence and mature protein", J. Bacteriol. 159: 811 (1984).

Yang et al, "Cloning of the neutral protease gene of *Bacillus subtilis* and the use of the cloned gene to create an in vitro–derived del etion mutation", J. Bacteriol. 160: 15 (1984).

Chang et al, "Expression of eukaryotic genes in B. subtilis using signals of penP", in Molecular Cloning and Gene Regulation in Bacilli, 1982, Ganesan et al (ed.), Academic Press, New York, pp. 159–169.

Molecular Cloning, A Laboratory Manual, 1982, Maniatis et al, Cold Spring Harbor Laboratory, Cold Spring Harbor, New York, pp. 3–5, 51, 52, and 270–274.

Takagi, Experimental Methods for Gene Manipulation, p. 139, lines 10–13.

Horinouchi, "Expression of Information in Gram–positive Bacteria", Tanpakushitu–Kakusan–Koso, 28, (1468, lines 1–14, Abstract; p. 1468, left column, line 1—right column, line 17; p. 1468, right column, line 18—p. 1470, left column, line 21; p. 1470, right column, line 13—p. 1472, left column, line 13; and Figures 1–5).

Koch, in Manual of Methods for General, 1981, Gerhardt et al (ed.), American Society for Microbiology, Washington, DC, pp. 179, 195, 196, and 197.

Physical Biochemistry, 1982, Friefelder, W.H. Freeman and Co., New York, NY, pp. 504–506.

FIG. 1(a)

```
                  20                              40
GATCTTAACATTTTTCCCCT              ATCATTTTTCCCGTCTTCAT
                  60                              80
TTGTCATTTTTTCCAGAAAA              AATCGTCATTCGACTCATGT
                 100                             120
CTAATCCAACACGTCTCTCT              CGGCTTATCCCCTGACACCG
                 140                             160
CCCGCCGACAGCCCGCATGG              ACGAATCTATCAATTCAGCC
                 180                             200
GCGGAGTCTAGTTTTATATT              GCAGAATGCGAGATTGCTGG
                 220                             240
TTTATTATAACAATATAAGT              TTTCATTATTTTCAAAAAGG
                                      ++++
                 260                             280
GGGATTTATTGTGGGTTTAG              GTAAGAAATTGTCTAGTGCT
+++
                 300                             320
GTAGCCGCTTCCTTTATGAG              TTTAACCATCAGTCTGCCGG
                 340                             360
GTGTTCAGGCCGCTGAGAAT              CCTCAGCTTAAAGAAAACCT
                 380                             400
GACGAATTTTGTACCGAAGC              ATTCTTTGGTGCAATCAGAA
                 420                             440
TTGCCTTCTGTCAGTGACAA              AGCTATCAAGCAATACTTGA
                 460                             480
AACAAAACGGCAAAGTCCTT              AAAGGCAATCCTTCTGAAAG
                 500                             520
ATTGAAGCTGATTGACCAAA              CGACCGATGATCTCGGCTAC
                 540                             560
AAGCACTTCCGTTATGTGCC              TGTCGTAAACGGTGTGCCTG
                 580                             600
TGAAAGACTCTCAAGTCATT              ATTCACGTCGATAAATCCAA
                 620                             640
CAACGTCTATGCGATTAACG              GTGAATTAAACAACGATGTT
                 660                             680
TCCGCCAAAACGGCAAACAG              CAAAAAATTATCTGCAAATC
                 700                             720
AGGCGCTGGATCATGCTTAT              AAAGCGATCGGCAAATCACC
                 740                             760
TGAAGCCGTTTCTAACGGAA              CCGTTGCAAACAAAAACAAA
                 780                             800
GCCGAGCTGAAAGCAGCAGC              CACAAAAGACGGCAAATACC
```

(Continued on the next page)

FIG. 1(b)

contd. from(a)

```
                820                              840
GCCTCGCCTATGATGTAACC            ATCCGCTACATCGAACCGGA
                860                              880
ACCTGCAAACTGGGAAGTAA            CCGTTGATGCGGAAACAGGA
                900                              920
AAAATCCTTGAAAAAGCAAA            ACAAAGTGGGCATGCCGCCA
                940                              960
CAACCGGAACAGGTACGACT            CTTAAAGGAAAAACGGTCTC
                980                             1000
ATTAAATATTTCTTCTGAAA            GCGGCAAATATGTGCTGCGC
               1020                             1040
GATCTTTCTAAACCTACCGG            AACACAAAATAATACGTACG
               1060                             1080
ATCTGCAAAACCGCGAGTAT            AACCTGCCGGGCACACTCGT
               1100                             1120
ATCCAGCACCACAAACCAGT            TTACAACTTCTTCTCAGCGC
               1140                             1160
GCTGCCGTTGATGCGCATAA            CAACCTCGGCAAAGTGTATG
               1180                             1200
AATATTTCTATCAGAAGTAT            AATCGCAACAGCTACGACAA
               1220                             1240
TAAAGGCGGCAAGATCGTAT            CCTCCGTTCAATACGGCAGC
               1260                             1280
AGATACAATAACGCAGCCTG            GATCGGCGACCAAATGATTT
               1300                             1320
ACGGTGACGGCGACGGTTCA            TTCTTCTCACCTCTTTCCGG
               1340                             1360
TTCAATGGACGTAACCGCTC            ATGAAATGACACATGGCGTT
               1380                             1400
ACACAGGAAACAGCCAACCT            GAACTACGAAAATCAGCCGG
               1420                             1440
GCGCTTTAAATGAATCATTC            TCTGATGTATTCGGGTACTT
               1460                             1480
CAACGATACTGAGGACTGGG            ATATCGGTGAAGATATTACG
               1500                             1520
GTCAGCCAGCCGGCTCTCCG            CAGCTTATCCAATCCGACAA
               1540                             1560
AATACGGACAGCCTGATAAT            TTCAAAAATTACAAAAACCT
               1580                             1600
TCCGAACACCGATGCCGGCG            ACTACGGCGGCGTGCATACA
```

(Continued on the next page)

FIG.1(C)

contd. from(b)

```
            1620                         1640
AACAGCGGAATCCCGAACAA     AGCCGCTTACAATACGATTA
            1660                         1680
CAAAAATCGGCGTGAACAAA     GCGGAGCAGATTTACTATCG
            1700                         1720
TGCTCTGACGGTATACCTCA     CTCCGTCATCAACTTTTAAA
            1740                         1760
GATGCAAAAGCCGCTTTGAT     TCAATCTGCGCGGGACCTTT
            1780                         1800
ACGGCTCTCAAGATGCTGCA     AGGCTAGAAGCTGCCTGGAA
            1820                         1840
TGCAGTCGGATTGTAAACAA     GAAAAGAGACCGGAAATCCG
            1860                         1880
GTCTCTTTTTTATATCTAAA     AACATTTCACAGTGGCTTCA
            1900
CCATGATC
```

FIG. 2

1  2  3   4   5   6   7   8   9   10  11  12  13
ALA-ALA-THR-THR-GLY-THR-GLY-THR-THR-LEU-LYS-GLY-LYS

FIG. 3

1  2  3   4   5   6   7   8   9   10  11  12  13
ALA-ALA-ALA-THR-GLY-SER-GLY-THR-THR-LEU-LYS-GLY-ALA

DNA BASE SEQUENCE CONTAINING REGIONS INVOLVED IN THE PRODUCTION AND SECRETION OF A PROTEIN, RECOMBINANT DNA INCLUDING THE WHOLE OR A PART OF THE DNA BASE SEQUENCE, AND METHOD OF PRODUCING PROTEINS BY USE OF THE RECOMBINANT DNA

This is a continuation of prior U.S. application Ser. No. 07/988,015 Filing Date Dec. 09, 1992, now abandoned and/which is a continuation of application Ser. No. 07/628,989 Filing Date Dec. 17, 1990, now abandoned and/which is a continuation of application Ser. No. 07/159,513 Filing Date Feb. 19, 1988, now abandoned and/which is a continuation of application Ser. No. 06/686,892 Filing Date Dec. 12, 1984, now abandoned.

BACKGROUND OF THE INVENTION

1. Field of the Invention

This invention relates to a DNA base sequence which contains regions involved in the production and secretion of a protein, a recombinant DNA which includes the whole or a part of the DNA base sequence, and a method of producing proteins which comprises introducing the recombinant DNA into a microorganism, culturing this microorganism and thereby causing the protein to be extracellularly secreted in large amounts, and then recovering the protein.

2. Description of the Prior Act

Bacteria of the genus Bacillus are known to secrete a variety of proteins extracellularly. Among others, neutral protease is one of the most useful enzymes that are currently produced on an industrial scale, and its wide field of application covers, for example, the manufacture of foods and cosmetics, the tanning of hides and the production of dry cleaning soap. Conventionally, neutral protease has been obtained by culturing a bacterium which is highly productive of this enzyme (such as *B. amyloliquefaciens*, *B. subtilis*, *B. sacchariticus* or *B. licheniformis*), collecting the cell-free culture medium which contains neutral protease, and separating the enzyme into a purified form. However, in addition to neutral protease, Bacillus bacteria secrete and accumulate a large amount of other extracellular proteins (such as amylase, alkaline protease and levansucrase) in the cell-free culture medium. Accordingly, in the production of neutral protease, much effort has been required to remove such contaminants.

As an effective means of overcoming this disadvantage, attention is being given to the microbial production of proteins by utilizing the cloning technique in which a gene coding for a desired protein is combined with a suitable vector and the resulting recombinant DNA is introduced into a host bacterium to transform it.

More specifically, a DNA fragment which contains regions involved in the production and secretion of a desired protein is isolated and combined with a suitable vector to form a recombinant DNA which permits the genetic information concerning the production and secretion of the protein to be expressed in host cells. Then, this recombinant DNA is introduced into a suitable host bacterium, which is cultured to cause the protein to be secreted in large amounts. Thus, the protein can be recovered from the cell-free culture medium according to a simple procedure.

The DNA fragment used for forming the recombinant DNA obtained by the above-described method must contain regions which are involved in the production and secretion of the desired protein, that is, the promoter region, the ribosome binding region, the structural gene for the desired protein, and the terminator region.

The regions involved in the expression of the gene include the promoter region which has the −35 and −10 regions which act as RNA polymerase recognition and binding sites; and the ribosome binding region which defines the base sequence through which the messenger RNA synthesized by RNA polymerase binds ribosomes. The base sequences of these regions are very important for the efficiency of the gene expression. In addition, the distance (i.e., the number of bases) between these regions is also known to be very important [Moran, Jr., et al., Mol. Gen. Genet., 186, 339(1982)].

In the extracellular secretion of the protein synthesized in the cells as a result of gene expression, the region which codes for the polypeptide chain upstream of the amino end of the protein secreted extracellularly as mature protein is important. The protein newly synthesized in the cells has this polypeptide chain in the form combined with the amino end of the mature protein, but as soon as the polypeptide chain is removed by the action of peptidase, the newly synthesized protein is extracellularly secreted to provide mature protein. Accordingly, the region of the gene which codes for the polypeptide chain is essential to the secretion of the protein synthesized as a result of gene expression.

Moreover, it is desirable from the viewpoint of the industrial production of proteins that the DNA fragment which is used for forming the recombinant DNA have the characteristics which permit a high-level expression of the gene and efficient secretion of the protein.

Thus, in the industrial production of proteins which use the genetic engineering techniques explained thus far, it is very important to clone a DNA fragment which is a chromosome segment which has the structural gene for a desired protein and regions which are involved in the expression of the gene and the secretion of the resulting protein, to isolate the DNA fragment in a pure form, determine its DNA base sequence, and apply it to practical uses.

Bacteria of the genus Bacillus are preferred as host microorganisms from an industrial point of view, because they lack pathogenicity, can be easily handled and cultured, and have long been used in fermentation technology (Debabov, "The Molecular Biology of the Bacilli", 1 332(1982), Dubnau, D. A., ed., Academic Press).

However, where a foreign gene is to be expressed in host bacilli, the RNA polymerase and ribosomes of bacilli have rigid specificity in relation to the recognition of the promoter region and the ribosome binding region [Sueji Horinouchi, Tanpakushitsu-Kakusan-Koso, 28, 1468(1983)], so that these regions must be derived from bacilli [Goldfarb, D. S., et al., Nature, 293, 309(1981)].

From this point of view, an attempt has been made to produce foreign proteins by combining a foreign gene with a DNA base sequence which contains the promoter and ribosome binding regions specific for bacilli and allowing this recombinant DNA to be expressed in a host bacillus [Williams, D. M., et al., Gene, 16, 199 (1981)]. Moreover, an effort has also been made to obtain powerful promoter regions and signal sequences for extracellularly secreted enzymes of bacilli [Palva, I., et al., Gene, 15, 43 (1981)].

However, in preparing DNA fragments for use in the formation of recombinant DNA molecules which contain regions involved in the production and secretion of, for example, neutral protease and particularly its powerful promoter region and signal sequence, it becomes difficult to form recombinant DNA molecules which comprise DNA fragments combined with a vector if the size of the chromosome segments obtained by cleaving the chromosomes isolated from a donor microorganism exceeds a certain limit [Takagi Y., ed., "Experimental Methods for Gene Manipulation", p. 139, Kodansha (1980)]. Even if chromosome segments of such an exceedingly large size can be combined with a vector to form recombinant DNA molecules, these recombinant DNA molecules cannot be stably retained within host cells, so that it is impossible to obtain the desired DNA segment by cloning. Thus, it is necessary to select a restriction enzyme which can yield chromosome segments of proper size.

However, no restriction enzyme that is suitable for this purpose and which can be successfully used in combination with the chromosomes isolated from a donor microorganism is known as yet.

Even in the case of restriction enzymes which have a cleavage site in the structural gene for neutral protease or its promoter region or signal sequence, they can theoretically be used if the chromosomes are treated under partial cleavage conditions. However, if a plurality of such cleavage sites is present in the DNA fragment, the fragment will unavoidably be cleaved at some of those sites, thus making it difficult to clone the DNA fragment.

SUMMARY OF THE INVENTION

It is an object of the present invention to provide a DNA base sequence which contains regions involved in the production and secretion of a protein as well as its derivative sequences and, in particular, a DNA base sequence which contains regions involved in high-level expression of a gene and efficient secretion of the resulting protein in bacteria of the genus Bacillus as well as its derivative sequences.

It is another object of the present invention to provide a recombinant DNA which includes the whole or a part of the DNA base sequence.

It is still another object of the present invention to provide a method of producing proteins in which a microorganism which has the recombinant DNA introduced thereinto is cultured to yield the desired protein which corresponds to the structural gene included in the introduced recombinant DNA.

These objects of the present invention can be accomplished by (a) a DNA base sequence in which one of the strands comprises bases arranged in the following order:

```
         20                        40
GATCTTAACATTTTTCCCCT      ATCATTTTTCCCGTCTTCAT
         60                        80
TTGTCATTTTTCCAGAAAA       AATCGTCATTCGACTCATGT
        100                       120
CTAATCCAACACGTCTCTCT      CGGCTTATCCCCTGACACCG
        140                       160
CCCGCCGACAGCCCGCATGG      ACGAATCTATCAATTCAGCC
        180                       200
GCGGAGTCTAGTTTTATATT      GCAGAATGCGAGATTGCTGG
        220                       240
TTTATTATAACAATATAAGT      TTTCATTATTTTCAAAAAGG
        260                       280
GGGATTTATTGTGGGTTTAG      GTAAGAAATTGTCTAGTGCT
        300                       320
GTAGCCGCTTCCTTTATGAG      TTTAACCATCAGTCTGCCGG
        340                       360
GTGTTCAGGCCGCTGAGAAT      CCTCAGCTTAAAGAAAACCT
        380                       400
GACGAATTTTGTACCGAAGC      ATTCTTTGGTGCAATCAGAA
        420                       440
TTGCCTTCTGTCAGTGACAA      AGCTATCAAGCAATACTTGA
        460                       480
AACAAAACGGCAAAGTCCTT      AAAGGCAATCCTTCTGAAAG
        500                       520
ATTGAAGCTGATTGACCAAA      CGACCGATGATCTCGGCTAC
        540                       560
AAGCACTTCCGTTATGTGCC      TGTCGTAAACGGTGTGCCTG
        580                       600
TGAAAGACTCTCAAGTCATT      ATTCACGTCGATAAATCCAA
        620                       640
CAACGTCTATGCGATTAACG      GTGAATTAAACAACGATGTT
        660                       680
TCCGCCAAAACGGCAAACAG      CAAAAAATTATCTGCAAATC
        700                       720
AGGCGCTGGATCATGCTTAT      AAAGCGATCGGCAAATCACC
        740                       760
TGAAGCCGTTTCTAACGGAA      CCGTTGCAAACAAAAACAAA
        780                       800
GCCGAGCTGAAAGCAGCAGC      CACAAAAGACGGCAAATACC
        820                       840
GCCTCGCCTATGATGTAACC      ATCCGCTACATCGAACCGGA
        860                       880
ACCTGCAAACTGGGAAGTAA      CCGTTGATGCGGAAACAGGA
        900                       920
AAAATCCTTGAAAAAGCAAA      ACAAAGTGGGCATGCCGCCA
        940                       960
CAACCGGAACAGGTACGACT      CTTAAAGGAAAAACGGTCTC
        980                       1000
ATTAAATATTTCTTCTGAAA      GCGGCAAATATGTGCTGCGC
       1020                       1040
GATCTTTCTAAACCTACCGG      AACACAAAATAATACGTACG
       1060                       1080
ATCTGCAAAACCGCGAGTAT      AACCTGCCGGGCACACTCGT
       1100                       1120
ATCCAGCACCACAAACCAGT      TTACAACTTCTTCTCAGCGC
       1140                       1160
GCTGCCGTTGATGCGCATAA      CAACCTCGGCAAAGTGTATG
       1180                       1200
AATATTTCTATCAGAAGTAT      AATCGCAACAGCTACGACAA
       1220                       1240
TAAAGGCGGCAAGATCGTAT      CCTCCGTTCAATACGGCAGC
       1260                       1280
AGATACAATAACGCAGCCTG      GATCGGCGACCAAATGATTT
       1300                       1320
ACGGTGACGGCGACGGTTCA      TTCTTCTCACCTCTTTCCGG
       1340                       1360
TTCAATGGACGTAACCGCTC      ATGAAATGACACATGGCGTT
       1380                       1400
ACACAGGAAACAGCCAACCT      GAACTACGAAAATCAGCCGG
```

-continued

```
                1420                        1440
GCGCTTTAAATGAATCATTC    TCTGATGTATTCGGGTACTT
                1460                        1480
CAACGATACTGAGGACTGGG    ATATCGGTGAAGATATTACG
                1500                        1520
GTCAGCCAGCCGGCTCTCCG    CAGCTTATCCAATCCGACAA
                1540                        1560
AATACGGACAGCCTGATAAT    TTCAAAAATTACAAAAACCT
                1580                        1600
TCCGAACACCGATGCCGGCG    ACTACGGCGGCGTGCATACA
                1620                        1640
AACAGCGGAATCCCGAACAA    AGCCGCTTACAATACGATTA
                1660                        1680
CAAAAATCGGCGTGAACAAA    GCGGAGCAGATTTACTATCG
                1700                        1720
TGCTCTGACGGTATACCTCA    CTCCGTCATCAACTTTTAAA
                1740                        1760
GATGCAAAAGCCGCTTTGAT    TCAATCTGCGCGGGACCTTT
                1780                        1800
ACGGCTCTCAAGATGCTGCA    AGGCTAGAAGCTGCCTGGAA
                1820                        1840
TGCAGTCGGATTGTAAACAA    GAAAAGAGACCGGAAATCCG
                1860                        1880
GTCTCTTTTTTATATCTAAA    AACATTTCACAGTGGCTTCA
                1900
CCATGATC
``` where A, T, G and C represent adenine, thymine, guanine and cytosine, respectively, or a derivative sequence thereof;

(b) a recombinant DNA which includes the whole or a part of the above mentioned DNA base sequence or a derivative sequence thereof;

and (c) a method of producing proteins which comprises introducing the aforesaid recombinant DNA into a host microorganism, culturing this host microorganism and thereby causing the desired protein coded for by the structural gene included in the recombinant DNA to be produced and secreted extracellularly in large amounts, and then recovering the protein.

BRIEF DESCRIPTION OF THE DRAWINGS

FIG. 1(a)–(c) is a diagram which shows the DNA base sequence of the present invention which contains the neutral protease gene of *Bacillus amyloliquefaciens*. In this DNA base sequence, segment 179–184 represents the –35 region, segment 203–208 represents the –10 region, segment 236–243 represents the ribosome binding region, segment from 251 represents the region involved in the secretion of the protein, segment 914–1813 represents the region coding for the mature protein, and segment 1820–1851 represents the part which includes the terminator region. In FIG. 1 (a)–(c), A, T, G and C represent adenine, thymine, guanine and cytosine, respectively. Furthermore, on the underside of the DNA base sequence, the –35 region in the promoter region is expressed by ____, the –10 region in the promoter region by ====, the ribosome binding region by ++++++, the start of the region involved in the secretion of the protein by ~~~~, the region coding for the mature protein by ----><-----, the protein transcription termination coding by ***, and the terminator region by —><—.

FIG. 2 is a diagram which shows the amino acid sequence of the amino end portion of extracellular neutral protease produced by *Bacillus amyloliquefaciens* and strain MT-0150.

FIG. 3 is a diagram which shows the amino acid sequence of the amino end portion of extracellular neutral protease produced by *Bacillus subtilis*.

DETAILED DESCRIPTION OF THE PREFERRED EMBODIMENTS

As a result of investigation using a variety of restriction enzymes, the present inventors have found that a DNA fragment which contains the structural gene for neutral protease and its promoter region and signal sequence can be obtained from donor chromosomes under the conditions of partial cleavage with the restriction enzyme Sau3AI and that the size of this DNA fragment is as small as 1.7 kb and, therefore, a recombinant DNA molecule formed by combining it with a vector can be retained in host cells which makes it possible to obtain a large amount of purified DNA fragment by cloning. Furthermore, the present inventors have analyzed the base sequence of the resulting DNA fragment to identify the fragment, and thereby completed the present invention.

The DNA base sequence of the present invention contains regions involved in the production of a protein by microorganisms and the extracellular secretion of the protein and, in particular, regions involved in the production and secretion of neutral protease.

More specifically, the DNA base sequence of the present invention contains one or more regions selected from the group which consists of the promoter region, the ribosome binding region, the region involved in the extracellular secretion of the protein, the structural gene and the terminator region, all are of the neutral protease gene.

The specific form of the DNA base sequence of the present invention which contains all of the aforesaid regions is shown in FIG. 1.

The regions involved in the expression of the gene include the promoter region which has the –35 and –10 regions which act as RNA polymerase recognition and binding sites; and the ribosome binding region which defines the base sequence with which the messenger RNA synthesized by the RNA polymerase binds ribosomes. The base sequences of these regions are very important for the efficiency of gene expression. In addition, the distances (i.e., the number of bases) between these regions are also known to be very important [Moran, Jr., et al., Mol. Gen. Genet., 186, 339 (1982)]. The DNA base sequence of the present invention which is shown in FIG. 1 contains all of these regions and, therefore, is considered to be essential to the expression of the neutral protease gene.

In the DNA base sequence of FIG. 1, the –35 region (____) and –10 regions (====) found in the promoter region are "TTGCAG" and "TATTAT", respectively, which resemble the sequences generally regarded as common [Sueji Horinouchi, Tanpakushitsu-Kakusan-Koso, 28, 1486(1983)]. In the present case, the ribosome binding region (++++++) is "AAAGGGGG", which differs by only one base from the sequence "AAAGGAGG", which is perfectly complementary to the ribosomal DNA of *Bacillus subtilis* [McLaughlin et al. "Unique Features in the Ribosmoe Binding Site Sequence of the Gram-positive *Staphylococcus aureus* β-Lactamase Gene" *The Journal of Biological Chemistry*, Vol. 256, No. 21 (Nov. 10, 1981). pp.

11283–11291.] Judging from these results, the neutral protease gene is believed to have very powerful promoter and ribosome binding regions.

The terminator region (→←) which shows the end of genetic information is also important for the efficiency of gene expression. The mRNA synthesis which started at the promoter region is thought to end at the terminator region located at the tail of the gene. In the present case, the existence of a DNA base sequence which serves to define a high order of structure of DNA and is considered to be the terminator region is noted at the tail of the neutral protease gene (FIG. 1).

The DNA base sequence of FIG. 1 in accordance with the present invention contains the structural gene (-----→←-----) which defines the mature neutral protease protein itself. Generally, an extracellularly secreted protein has an inherent amino acid sequence (known as the signal sequence) which takes part in its secretion, that is, the polypeptide chain located on the upstream side of the amino end of the protein which provides extracellularly accumulated mature protein [Tanpakushitsu-Kakusan-Koso, 26, 2044(1981)]. The neutral protease defined by the DNA base sequence of the present invention is also a protein which is efficiently secreted out of the cells. Accordingly, the above mentioned DNA base sequence likewise contains a region (from ∼∼∼∼) which carries genetic information concerning the extracellular secretion of the enzyme.

The region contained in the aforesaid DNA base sequence of the present invention and which carries genetic information concerning the secretion of the protein is believed to be effective beyond the species of the genus Bacillus because, when the neutral protease gene of *Bacillus amyloliquefaciens* which has the DNA base sequence of the present invention is cloned in *Bacillus subtilis* which is used as the host, a very large amount of neutral protease is secreted and accumulated in a short period of time.

Thus, the DNA base sequence of the present invention which has been described above with reference to FIG. 1 is involved in high-level expression of the gene and efficient secretion of the protein thus synthesized, and has an important significance in the production by Bacillus bacteria of proteins which are foreign gene products.

More specifically, since the DNA base sequence of the present invention contains the promoter and ribosome binding regions which are capable of bringing about high-level expression of the gene, and also contains the region involved in efficient secretion of the resulting protein, it is possible to combine a desired foreign gene (e.g., any of the structural genes for interferon, growth hormone, interleukin, nerve growth factor, kallikrein, plasminogen activator, and other physiologically active polypeptides or enzymes) on the downstream side of this DNA base sequence and introduce it into a host bacterium of the genus Bacillus, thereby causing the corresponding protein to be efficiently secreted and accumulated outside of the cells.

Moreover, the base sequences of the promoter and ribosome binding regions involved in the expression of the gene and the base sequence of the region involved in the secretion of the resulting protein can be cut out of the DNA base sequence of the present invention and used alone or in any combination to produce good results in the expression of the gene and/or the secretion of the protein. Furthermore, these regions can also be synthesized and used to produce good results. Thus, the DNA base sequence of the present invention has an important significance in the production of proteins which originate from foreign genes.

It is obvious that, if DNA base sequences are prepared by substituting the DNA base sequence of the present invention in such a way that the amino acid sequence defined by the region located downstream of the ribosome binding region and coding for a protein remains unchanged, the proteins synthesized by the expression of these substituted DNA base sequences are identical with the protein coded for by the DNA base sequence of the present invention and hence have all the same functions as the latter. Naturally, such DNA base sequences also fall within the scope of the present invention. In addition, derivative sequences which are obtained by subjecting an arbitrarily selected portion of the DNA base sequence of the present invention to base substitution, insertion, deletion, or transposition also fall within the scope of the present invention, provided that they retain the characteristics (which constitute the main features of the present invention) of the promoter or ribosome binding region or the region involved in the secretion of the protein, that is, high-level expression of the gene or efficient secretion of the resulting protein.

A DNA fragment which has the DNA base sequence of FIG. 1 in accordance with the present invention can be obtained by isolating chromosomes from a microorganism which has the ability to secrete neutral protease extracellularly in large amounts, and cleaving these chromosomes by means of a suitable restriction enzyme.

Especially when it is desired to produce neutral protease by introducing the DNA fragment into a host bacterium of the genus Bacillus, the DNA fragment is preferably derived from any of the Bacillus bacteria that can produce neutral protease which has the amino acid sequence defined by the DNA base sequence of the present invention. Particularly preferred are bacteria of the genus Bacillus which can produce the enzyme in large amounts and have the DNA base sequence of the present invention in their chromosomes. Examples of such bacteria include *Bacillus amyloliquefaciens*, *B. subtilis*, *B. licheniformis*, *B. cereus* and *B. megaterium*.

Chromosomes can be isolated from a donor microorganism according to the method of Marmur [Marmur, J. J., Mol. Biol., 3, 208(1961)] or the method of Saito and Miura [Saito, H., and Miura, K-I., Biochim. Biophys. Acta, 72, 619(1963)], though any other method may be employed. The chromosomal DNA thus obtained is cleaved by means of a restriction enzyme. Theoretically, there may be used any restriction enzyme that does not cleave the structural gene for neutral protease or its promoter region or signal sequence. However, as previously described, it becomes difficult to form recombinant DNA molecules which comprise DNA fragments combined with a vector if the size of the resulting chromosome segments exceeds a certain limit. Even if chromosome segments of such an exceeding large size can be combined with a vector to form recombinant DNA molecules, these recombinant DNA molecules cannot be stably retained within host cells, so that it is impossible to obtain the desired DNA fragment by cloning.

Even in the case of restriction enzymes which has a cleavage site in the structural gene for neutral protease or its promoter region or signal sequence, they can theoretically be used if the chromosomes are treated under partial cleavage conditions. However, if a plurality of such cleavage sites is present in the DNA fragment, it will unavoidably be cleaved at some of those sites, thus making it difficult to clone the DNA fragment.

Accordingly, it is preferable to use a restriction enzyme which permits a DNA fragment which has the DNA base sequence of FIG. 1 in accordance with the present invention to be cut out of the chromosomes under partial cleavage conditions in the form of a short segment. An example of such a restriction enzyme is Sau3AI.

(Recombinant DNA)

The expression "recombinant DNA including the DNA base sequence of the present invention" as used herein means any recombinant DNA obtained by combining vector DNA with a DNA fragment which has the whole or a part of the DNA base sequence of the present invention which contains the neutral protease gene. In this connection, such recombinant DNAs can be obtained not only by combining a DNA fragment which has the DNA base sequence of the present invention with an extranuclear genetic element (such as a plasmid, phage or cosmid) which is capable of being retained within bacterial cells, but also by inserting a DNA fragment which includes the DNA base sequence of the present invention into the chromosomal DNA of a host microorganism through, for example, intracellular recombination. It is to be understood that all such recombinant DNAs fall within the scope of the present invention.

The recombinant DNAs of the present invention can be obtained according to the genetic engineering technique known as cloning.

In the practice of the present invention, it is suitable for the intended purpose of the present invention to use as the vector DNA a plasmid or phase which is capable of being retained within bacterial cells, because this results in a large number of copies of the DNA fragment which include the DNA base sequence. In other words, the presence of a large number of copies of the DNA fragment in bacterial cells makes it possible to produce neutral protease in large amounts and, moreover, to recover the DNA fragment in large amounts, thereby facilitating the improvement of neutral protease at the DNA level.

For purposes of cloning, there may be used any vector that is capable of amplification in host cells. However, the use of vectors which have a single cleavage site for the restriction enzyme BamHI, BglII or Sau3AI is convenient for the preparation of recombinant DNA molecules by combining them with the above mentioned DNA fragment. Examples of such vectors are plasmid pUB110 and complex plasmids which have whole or a part of their structure in cases where *Bacillus subtilis* is used as the host; and plasmid pBR322 and complex plasmids which have the whole or a part of their structure in cases where *Escherichia coli* is used as the host. In spite of the above description, phages in common use for purposes of cloning can also be used. Examples of such phages are λ phage and M13 phage in cases where *Escherichia coli* is used as the host, and p11 phage and φ105 phage in cases where *Bacillus subtilis* is used as the host. Any of the microorganisms (such as *Escherichia coli* and *Bacillus subtilis*) in common use for purposes of cloning may be used as the host, irrespective of its type. However, *Bacillus subtilis* is convenient for the selection of transformants because its strain which has been transformed by a recombinant DNA molecule which includes the DNA fragment can extracellularly secrete the neutral protease protein coded for by the DNA fragment.

Transformation can be carried out according to any of the commonly used methods. For example, where *Escherichia coli* is used as the host, there may be employed the method in which transformation is carried out in the presence of calcium ions [Mandel, M., and Higa, A., J. Mol. Biol., 53, 159(1970)] and its modification which uses rubidium [Bolivar, F., and Backman, K., Method in Enzymology, 68, p. 253, Academic Press (1979)]. Where *Bacillus subtilis* is used as the host, there may be employed the protoplast method [Chang, S., and Cohen, S. N., Mol. Gen. Genet., 168, 111(1978)], the competent cell method [Contente, S., and Dubnau, D., Mol. Gen. Genet., 167, 251(1979)] and the rescue method [Gryczan, T., et al., Mol. Gen. Genet., 177, 459(1980)]. However, any other method may be employed without being restricted to the aforesaid ones.

Where *Bacillus subtilis* is used as the host, transformants can be very easily selected by using a casein-containing agar medium and examining the presence or absence of a large halo formed around each colony. Where a Gram-negative microorganism such as *Escherichia coli* is used as the host, transformants can be selected, for example, by determining the protease activity with the aid of a bacteriolytic fluid or by using chloroform or the like to lyze the colonies formed on a casein-containing agar medium, incubating the medium at 37° C., and examining the formation of haloes.

In order to prepare the desired recombinant DNA molecule from the transformed strain thus obtained, any of the conventional methods for the preparation of plasmids or phage DNA may be employed. There is a considerable body of literature on these methods [Maniatis, T., et al., "Molecular Cloning", Cold Spring Harbor Laboratory (1982); Takagi Y., et al., "Manual for Gene Manipulation", Kodansha (1982)]. The recombinant DNA molecule thus obtained comprises the vector combined with a DNA fragment which has the desired structural gene for neutral protease and its promoter region and signal sequence.

By culturing a bacterium which has been transformed with the recombinant DNA of the present invention, the protein which corresponds to the recombinant DNA is produced in much larger amounts as compared with conventional methods. Although the term "protein" refers to neutral protease in the present case, it is natural that this term comprehends all proteins which correspond to DNA base sequences which are obtained by modifying a portion or portions of the DNA base sequence included in the recombinant DNA.

In carrying out the method of producing proteins in accordance with the present invention, a protein may be intracellularly or extracellularly produced by using a baterium which has been transformed with the recombinant DNA of the present invention. For example, a protein is intracellularly produced by using a bacterium which has been transformed with a recombinant DNA which includes the DNA base sequence which is deprived of the region involved in the secretion of the protein, and this method also falls within the scope of the present invention. However, if neutral protease is to be produced on an industrial scale, it is desirable for convenience of recovery and purification of the enzyme protein that the enzyme be secreted out of the productive bacterial cells, that is, into the culture medium. By transforming *Bacillus subtilis* with a recombinant DNA which includes the DNA base sequence of the present invention and culturing the transformed strain thus obtained, the present inventors succeeded in causing 50 times as much neutral protease to be secreted and accumulated in the culture medium as can be obtained with *Bacillus amyloliquefaciens* which is currently used in the industrial production of neutral protease. Neutral protease accounted for 95 percent of the protein secreted into the culture medium. As compared with the 60 percent observed in conventional methods, this value 95 percent is very favorable for the purpose of decreasing contamination with other proteins. These results have revealed that the neutral protease produced by the method of the present invention is very easy to purify.

The following examples are given to illustrate the method of preparing the DNA base sequence of the present invention which contains the neutral protease gene of *Bacillus amyloliquefaciens*, the method of determining the order of the bases in the DNA base sequence of the present invention, the method of preparing a recombinant DNA including the DNA base sequence of the present invention and using it to transform a bacterium, and the method of producing neutral protease by using the transformed strain. However, these examples are not to be construed to limit the scope of the present invention.

EXAMPLE 1

(Preparation of chromosomal DNA from *Bacillus amyloliquefaciens* and cleavage thereof with restriction enzymes)

*Bacillus amyloliquefaciens* strain F (Deposition No. ATCC 23350; a stock strain maintained in the American Type Culture Collection, 12301 Parklawn Drive, Rockville, Md. 20852-1776) was cultured in 2 liters of a broth medium (Difco Nutrient Broth) at 37° C. for 15 hours. Thereafter, the cells were collected and treated according to the method of Saito and Miura [Saito, H., and Miura, K-I., Biochem. Biophys. Acta, 72, 619(1963)] to obtain 10 mg of purified chromosomal DNA. Using 100 units of the restriction enzyme Sau3A (Takara Shuzo Co.), 500 µg of this chromosomal DNA was reacted at 37° C. for 5 minutes. In addition to Sau3A and DNA, the reaction system contained 7 mM $MgCl_2$ and 100 mM NaCl in a 10 mM Tris-HCl buffer solution (pH 7.5). After completion of the reaction, 1 µg of the DNA was analyzed by 1% agarose gel electrophoresis. This revealed that the reaction product was a partial degradation product of the donor chromosomes which was composed mainly of DNA fragments which had a size of 2–8 kb. Then, the remainder of the reaction product was subjected to electrophoresis in 0.7% low-melting agarose gel at 100 V for 3 hours. After the gel portion corresponding to a 1.5–9 kb fraction was cut out, DNA was isolated by extraction with phenol and with chloroform, and then recovered by precipitation with ethanol. The recovered DNA was dissolved in 200 µl of a 50 mM tris-HCl buffer solution (pH 7.5) and was used as donor chromosomal DNA fragments in the following experiment.

EXAMPLE 2

(Combination of donor chromosomal DNA fragments with a vector and transformation)

The donor chromosomal DNA fragments obtained in Example 1 were combined with plasmid pUB110 which had been completely cleaved by the restriction enzyme BamHI (Takara Shuzo Co.) and then treated with alkaline phosphatase of *Escherichia coli* (Worthington Co.) to hydrolyze its terminal phosphate.

More specifically, the treatment of pUB110 with BamHI was carried out by incubating the reaction system at 37° C. for 4 hours. The reaction system contained 100 µg of pUB110, 50 units of BamHI (Takara Shuzo Co.), 7 mM $MgCl_2$, 100 mM NaCl, 2 mM 2-mercaptoethanol and 0.01% bovine serum albumin in a 10 mM Tris-HCl buffer solution (pH 8.0). The resulting BamHI-cleaved pUB110 was extracted with phenol three times and then recovered by precipitation with ethanol. The recovered pUB110 was treated with alkaline phosphatase of *Escherichia coli* by dissolving it in a 0.1M Tris-HCl buffer solution (pH 8.0) which contained 5 units of BAPF (Worthington Co.) and incubating this reaction system at 65° C. for 4 hours. Thereafter, the resulting pUB110 was extracted with phenol and then recovered by precipitation with ethanol. The recovered pUB110 was dissolved in 100 µl of a 50 mM Tris-HCl buffer solution (pH 7.5).

Using $T_4$ ligase (Takara Shuzo Co.), the donor chromosomal DNA fragments which were obtained in Example 1 were combined with the BamHI- and phosphatase-treated pUB110. The reaction system contained 50 µl of the donor chromosomal DNA fragments, 20 µl of pUB110, 5 units of $T_4$ ligase, 6.6 mM $MgCl_2$, 10 mM dithiothreitol and 1 mM ATP (adenosine triphosphate) in a 66 mM Tris-HCl buffer solution (pH 7.5). The reaction was carried out at 15° C. for 4 hours. After completion of the reaction, a sample was analyzed by 1% agarose gel electrophoresis. This revealed that pUB110 used as the vector was combined with the donor chromosomal DNA segments to form recombinant DNA molecules.

Using the recombinant DNA molecules thus obtained, transformation was carried out according to the protoplast method of Chang [Chang, S., and Cohen, S. N., Mol. Gen. Genet., 168, 111(1978)]. The protoplasts were regenerated in a medium containing kanamycin sulfate at a final concentration of 100 µg/ml. As the host for cloning, there was used *Bacillus subtilis* strain 1A274 (a stock strain maintained in the Bacillus Genetic Stock Center, Department of Microbiology, the Ohio State University, 484 West, 12th Avenue, Coloumbus, Ohio 43210, U.S.A.).

The kanamycin-resistant strains obtained by the transformation were inoculated onto the TBAB agar media (Difco) containing 0.8% casein and 40 µg/ml kanamycin, incubated at 37° C. for 14 hours and then examined for the presence of a halo around each colony. Among about ten thousand kanamycin-resistant strains tested, one strain (#150) formed a significantly large halo around the colony.

EXAMPLE 3

(Preparation of a recombinant DNA molecule from the transformed strain and confirmation of the inclusion of the neutral protease gene of the donor)

The large halo forming strain obtained by isolating the single colony of the transformed strain #150 described in Example 2 was cultured in 50 ml of the Pen Assay medium (Difco) at 37° C. for 14 hours. Thereafter, the cells were collected, washed with a 50 mM Tris-HCl buffer solution (pH 7.5) containing 5 mM EDTA and 50 mM NaCl, and then used in the preparation of a plasmid by the alkali method [Birnboim, H. C., and Poly, J., Nucleic Acid Res., 7, 1513(1979)]. The resulting plasmid was treated with the restriction enzymes EcoRI, BglII and BamHI, and then analyzed by 1% agarose gel electrophoresis. This revealed that EcoRI and BglII cleaved the plasmid at a single site to give a product having a size of 6.2 kb while BamHI did not cleave it. Since pUB110 used as the vector has a size of 4.5 kb and is cleaved by EcoRI, BglII and BamHI at a single site, the plasmid obtained from the large halo forming strain was found to be a recombinant DNA molecule which had a donor chromosomal DNA fragment of about 1.7 kb size inserted into the BamHI-cleaved site of pUB110. This recombinant plasmid was named pNP150.

The recombinant plasmid pNP150 thus obtained was used to transform *Bacillus subtilis* strain 1A20 (a stock strain maintained at the Bacillus Genetic Stock Center, the Ohio State University) by the competent cell method. This was carried out according to the procedure of Anagnostopoulos and Spizizen [Anagnostopoulos, C., and Spizizen, J. J., Bacteriol., 81, 741(1961)]. After about 5 µg of the recombinant DNA molecule was incorporated, 50 μl each of the culture medium (1 ml) was plated onto the TBAB agar medium which contained 0.8% casein and 40 μg/ml kanamycin. All of the resulting kanamycin-resistant transformants formed a large halo. This transformed strain MT-0150 (Deposition No. FERM BP-425; a stock strain maintained at the Fermentation Research Institute, Agency of Industrial Science and Technology, 1-1-3, Higashi 1-chome, Yatabe-Machi, Tsukuba gun, Ibaraki-ken 305, Japan) was cultured in a Pen Assay medium at 37° C. for 8 hours and the protease activity of the cell-free culture medium was determined according to the casein decomposition method ["Experimental Agricultural Chemistry", p. 284, Asakura Shuppan (1978)]. As a result, it became apparent that this transformed strain secreated 50 times as much neutral protease as *Bacillus amyloliquefaciens* (Table 1). Separately, the above mentioned cell-free culture medium was analyzed by an immunological double diffusion process which used antisera against the neutral proteases of *Bacillus amyloliquefaciens* and *Bacillus subtilis*. Thus, the neutral protease secreted by this transformed strain was found to be of the *Bacillus amyloliquefaciens* type. Moreover, the neutral protease secreted by the transformed strain MT-0150 and the extracellular neutral proteases of *Bacillus amyloliquefaciens* and *Bacillus subtilis* were recovered from the respective cell-free culture media. After these neutral proteases were purified, the amino acid sequence of their amino end was determined. This also revealed that the neutral protease produced by the transformed strain MT-0150 was not of the *Bacillus subtilis* type (as shown in FIG. 3) but of the *Bacillus amyloliquefaciens* type (as shown in FIG. 2). Furthermore, since the mature protein of the neutral protease originating from the gene of *Bacillus amyloliquefaciens* and produced in large amounts by the transformed strain MT-0150 had the same amino end as that of *Bacillus amyloliquefaciens*, the region contained in the neutral protease gene of *Bacillus amyloliquefaciens* and involved in the secretion of the protein was found to perform its proper function beyond the species of the genus Bacillus.

EXAMPLE 4

(Mass preparation of the neutral protease gene of *Bacillus amyloliquefaciens* and determination of its DNA base sequence)

The transformed *Bacillus subtilis* strain MT-0150 which was obtained in Example 3 and which had the DNA base sequence of the present invention was cultured in 5 liters of a broth medium (Difco Nutrient Broth) at 37° C. for 14 hours and the resulting cells were treated according to the method of Gryczan [Gryczan, T. J., J. Bacteriol., 134, 318(1978)] to obtain 2 mg of a purified plasmid (pNP150) which had the DNA base sequence of the present invention. Then, the base sequence of the inserted DNA fragment of the resulting plasmid pNP150 which included the neutral protease gene was determined according to the method of Maxam and Gilbert [Maxam, A., and Gilbert, W., Proc. Natl. Acad. Sci. USA, 74, 560(1977)].

FIG. 1 is a diagrammatic illustration of the DNA base sequence so determined. As can be seen from this figure, the entire amino acid sequence of neutral protease of *Bacillus amyloliquefaciens* has been elucidated for the first time.

On the upstream side of the structural gene, there may be seen the promoter region necessary for the expression of the gene and, in particular, the so-called −35 and −10 regions acting as RNA polymerase recognition and binding sites. The ribosome binding region is noted downstream of the promoter region, and an open reading frame coding for the protein begins at the protein synthesis initiation site located several bases downstream of the ribosome binding region. Of this open reading frame, the region coding for the polypeptide chain upstream of the amino end of the neutral protease includes an important part involved in the secretion of the protein, though that polypeptide chain will be removed during the secretion of the protein.

On the downstream side of the termination coding showing the end of the open reading frame, there may be seen a DNA base sequence capable of defining a secondary structure and considered to be the terminator region. Thus, it was confirmed that the recombinant plasmid pNP150 included the whole of the neutral protease gene.

EXAMPLE 5

(Production of neutral protease by use of the transformed strain)

The *Bacillus subtilis* strain MT-0150 obtained in Example 3 and which has the DNA base sequence of the present invention was cultured in 5 liters of a broth medium (Difco Nutrient Broth) at 37° C. for 14 hours. When determined according to the method described in Example 3, the cell-free culture medium exhibited a high protease activity and more than 95% of the activity was accounted for by neutral protease. *Bacillus subtilis* used as the host scarcely produced protease under these conditions, whereas the strain MT-0150 gave 50 times as high a value as *Bacillus amyloliquefacience* used as the DNA donor (Table 1).

Neutral protease was purified in the usual manner. More specifically, the cell-free culture medium was collected and precipitated with ammonium sulfate (75% saturation) and then with acetone (30–70% fraction). The 30–70% fraction with aceton was subjected to column chromatography using CM-Sepharose (Pharmacia Fine Chemicals). As a result, there was obtained a homogeneous protein. With conventional strains yielding a large amount of contaminants such as amylase, levansucrase etc., it has been impossible to obtain a homogeneous enzyme protein by such a simple procedure. Currently, this enzyme is being produced on an industrial scale by culturing *Bacillus amyloliquefaciens* and then recovering neutral protease from the cell-free culture medium. It has now been found that the method of the present invention can increase its productivity by a factor of 50 at once.

TABLE 1

|  | B. amylo-liquefaciens | B. subtilis | B. subtilis strain MT-0150 |
| --- | --- | --- | --- |
| Total protease | 27.8 | 3.8 | 1496.0 |
| Neutral protease | 25.6 | 1.2 | 1472.0 |
| Alkaline protease | 6.8 | 1.4 | 0.2 |

Note: The activities are expressed in units. One unit is defined as the activity of each milliliter of an enzyme solution that decomposes milk casein to increase the absorbance at 275 nm of the reaction system by 0.01 in 1 minute. The bacilli were cultured in a broth medium at 37° C. for 14 hours. The enzymatic reaction was carried out at 30° C. Neutral protease activity was determined by adding 1 mM DFP (difluoro pyrocarbonate) to the reaction system so as to inhibit alkaline protease. Alkaline protease activity was determined by adding 20 mM EDTA (ethylenediaminetetraacetate) to the reaction system so as to inhibit neutral protease.

What is claimed is:

1. A recombinant DNA of about 6.4 kilobase pairs, comprising:
   (a) a vector DNA which can be retained in host cells, and
   (b) a DNA fragment which has a size of about 1.8 kilobase pairs, the DNA fragment inserted into said vector DNA having a DNA base sequence comprising a promotor region for RNA polymerase recognition and binding sites a ribosome binding region, a region encoding a peptide for extracellular secretion of neutral protease, a structural gene for the neutral protease and terminator region for showing an end of genetic information, all being of a neutral protease gene of *B. amyloliquefaciens*, Strain F.

2. The recombinant DNA as claimed in claim 1 wherein the DNA fragment comprises the DNA base sequence of:

```
        20                      40
GATCTTAACATTTTTCCCCT    ATCATTTTTCCCGTCTTCAT
        60                      80
TTGTCATTTTTTCCAGAAAA    AATCGTCATTCGACTCATGT
       100                     120
CTAATCCAACACGTCTCTCT    CGGCTTATCCCCTGACACCG
       140                     160
CCCGCCGACAGCCCGCATGG    ACGAATCTATCAATTCAGCC
       180                     200
GCGGAGTCTAGTTTTATATT    GCAGAATGCGAGATTGCTGG
       220                     240
TTTATTATAACAATATAAGT    TTTCATTATTTTCAAAAAGG
       260                     280
GGGATTTATTGTGGGTTTAG    GTAAGAAATTGTCTAGTGCT
       300                     320
GTAGCCGCTTCCTTTATGAG    TTTAACCATCAGTCTGCCGG
       340                     360
GTGTTCAGGCCGCTGAGAAT    CCTCAGCTTAAAGAAAACCT
       380                     400
GACGAATTTTGTACCGAAGC    ATTCTTTGGTGCAATCAGAA
       420                     440
TTGCCTTCTGTCAGTGACAA    AGCTATCAAGCAATACTTGA
       460                     480
AACAAAACGGCAAAGTCCTT    AAAGGCAATCCTTCTGAAAG
       500                     520
ATTGAAGCTGATTGACCAAA    CGACCGATGATCTCGGCTAC
       540                     560
AAGCACTTCCGTTATGTGCC    TGTCGTAAACGGTGTGCCTG
       580                     600
TGAAAGACTCTCAAGTCATT    ATTCACGTCGATAAATCCAA
       620                     640
CAACGTCTATGCGATTAACG    GTGAATTAAACAACGATGTT
       660                     680
TCCGCCAAAACGGCAAACAG    CAAAAAATTATCTGCAAATC
       700                     720
AGGCGCTGGATCATGCTTAT    AAAGCGATCGGCAAATCACC
       740                     760
TGAAGCCGTTTCTAACGGAA    CCGTTGCAAACAAAAACAAA
       780                     800
GCCGAGCTGAAAGCAGCAGC    CACAAAAGACGGCAAATACC
       820                     840
GCCTCGCCTATGATGTAACC    ATCCGCTACATCGAACCGGA
       860                     880
ACCTGCAAACTGGGAAGTAA    CCGTTGATGCGGAAACAGGA
       900                     920
AAAATCCTTGAAAAAGCAAA    ACAAAGTGGGCATGCCGCCA
       940                     960
CAACCGGAACAGGTACGACT    CTTAAAGGAAAAACGGTCTC
       980                    1000
ATTAAATATTTCTTCTGAAA    GCGGCAAATATGTGCTGCGC
      1020                    1040
GATCTTTCTAAACCTACCGG    AACACAAAATAATACGTACG
      1060                    1080
ATCTGCAAAACCGCGAGTAT    AACCTGCCGGGCACACTCGT
      1100                    1120
ATCCAGCACCACAAACCAGT    TTACAACTTCTTCTCAGCGC
      1140                    1160
GCTGCCGTTGATGCGCATAA    CAACCTCGGCAAAGTGTATG
      1180                    1200
AATATTTCTATCAGAAGTAT    AATCGCAACAGCTACGACAA
      1220                    1240
TAAAGGCGGCAAGATCGTAT    CCTCCGTTCAATACGGCAGC
      1260                    1280
AGATACAATAACGCAGCCTG    GATCGGCGACCAAATGATTT
      1300                    1320
ACGGTGACGGCGACGGTTCA    TTCTTCTCACCTCTTTCCGG
      1340                    1360
TTCAATGGACGTAACCGCTC    ATGAAATGACACATGGCGTT
      1380                    1400
ACACAGGAAACAGCCAACCT    GAACTACGAAAATCAGCCGG
      1420                    1440
GCGCTTTAAATGAATCATTC    TCTGATGTATTCGGGTACTT
      1460                    1480
CAACGATACTGAGGACTGGG    ATATCGGTGAAGATATTACG
      1500                    1520
GTCAGCCAGCCGGCTCTCCG    CAGCTTATCCAATCCGACAA
      1540                    1560
AATACGGACAGCCTGATAAT    TTCAAAAATTACAAAAACCT
      1580                    1600
TCCGAACACCGATGCCGGCG    ACTACGGCGGCGTGCATACA
      1620                    1640
AACAGCGGAATCCCGAACAA    AGCCGCTTACAATACGATTA
      1660                    1680
CAAAAATCGGCGTGAACAAA    GCGGAGCAGATTTACTATCG
      1700                    1720
TGCTCTGACGGTATACCTCA    CTCCGTCATCAACTTTTAAA
      1740                    1760
GATGCAAAAGCCGCTTTGAT    TCAATCTGCGCGGGACCTTT
      1780                    1800
ACGGCTCTCAAGATGCTGCA    AGGCTAGAAGCTGCCTGGAA
      1820                    1840
TGCAGTCGGATTGTAAACAA    GAAAAGAGACCGGAAATCCG
      1860                    1880
GTCTCTTTTTTATATCTAAA    AACATTTCACAGTGGCTTCA
      1900
CCATGATC.
```

3. The recombinant DNA as claimed in claim 1 wherein the DNA fragment comprises a DNA base sequence obtained by subjecting the DNA base sequence of:

```
       20                        40
GATCTTAACATTTTTCCCCT      ATCATTTTTCCCGTCTTCAT 60                        80
TTGTCATTTTTTCCAGAAAA      AATCGTCATTCGACTCATGT 100                       120
CTAATCCAACACGTCTCTCT      CGGCTTATCCCCTGACACCG 140                       160
CCCGCCGACAGCCCGCATGG      ACGAATCTATCAATTCAGCC 180                       200
GCGGAGTCTAGTTTTATATT      GCAGAATGCGAGATTGCTGG 220                       240
TTTATTATAACAATATAAGT      TTTCATTATTTTCAAAAAGG 260                       280
GGGATTTATTGTGGGTTTAG      GTAAGAAATTGTCTAGTGCT 300                       320
GTAGCCGCTTCCTTTATGAG      TTTAACCATCAGTCTGCCGG 340                       360
GTGTTCAGGCCGCTGAGAAT      CCTCAGCTTAAAGAAAACCT 380                       400
GACGAATTTTGTACCGAAGC      ATTCTTTGGTGCAATCAGAA 420                       440
TTGCCTTCTGTCAGTGACAA      AGCTATCAAGCAATACTTGA 460                       480
AACAAAACGGCAAAGTCCTT      AAAGGCAATCCTTCTGAAAG 500                       520
ATTGAAGCTGATTGACCAAA      CGACCGATGATCTCGGCTAC 540                       560
AAGCACTTCCGTTATGTGCC      TGTCGTAAACGGTGTGCCTG 580                       600
TGAAAGACTCTCAAGTCATT      ATTCACGTCGATAAATCCAA 620                       640
CAACGTCTATGCGATTAACG      GTGAATTAAACAACGATGTT 660                       680
TCCGCCAAAACGGCAAACAG      CAAAAAATTATCTGCAAATC 700                       720
AGGCGCTGGATCATGCTTAT      AAAGCGATCGGCAAATCACC 740                       760
TGAAGCCGTTTCTAACGGAA      CCGTTGCAAACAAAAACAAA 780                       800
GCCGAGCTGAAAGCAGCAGC      CACAAAAGACGGCAAATACC 820                       840
GCCTCGCCTATGATGTAACC      ATCCGCTACATCGAACCGGA 860                       880
ACCTGCAAACTGGGAAGTAA      CCGTTGATGCGGAAACAGGA 900                       920
AAAATCCTTGAAAAAGCAAA      ACAAAGTGGGCATGCCGCCA 940                       960
CAACCGGAACAGGTACGACT      CTTAAAGGAAAAACGGTCTC 980                      1000
ATTAAATATTTCTTCTGAAA      GCGGCAAATATGTGCTGCGC 1020                      1040
GATCTTTCTAAACCTACCGG      AACACAAAATAATACGTACG 1060                      1080
ATCTGCAAAACCGCGAGTAT      AACCTGCCGGGCACACTCGT 1100                      1120
ATCCAGCACCACAAACCAGT      TTACAACTTCTTCTCAGCGC
```

```
      1140                      1160
GCTGCCGTTGATGCGCATAA      CAACCTCGGCAAAGTGTATG 1180                      1200
AATATTTCTATCAGAAGTAT      AATCGCAACAGCTACGACAA 1220                      1240
TAAAGGCGGCAAGATCGTAT      CCTCCGTTCAATACGGCAGC 1260                      1280
AGATACAATAACGCAGCCTG      GATCGGCGACCAAATGATTT 1300                      1320
ACGGTGACGGCGACGGTTCA      TTCTTCTCACCTCTTTCCGG 1340                      1360
TTCAATGGACGTAACCGCTC      ATGAAATGACACATGGCGTT 1380                      1400
ACACAGGAAACAGCCAACCT      GAACTACGAAAATCAGCCGG 1420                      1440
GCGCTTTAAATGAATCATTC      TCTGATGTATTCGGGTACTT 1460                      1480
CAACGATACTGAGGACTGGG      ATATCGGTGAAGATATTACG 1500                      1520
GTCAGCCAGCCGGCTCTCCG      CAGCTTATCCAATCCGACAA 1540                      1560
AATACGGACAGCCTGATAAT      TTCAAAAATTACAAAAACCT 1580                      1600
TCCGAACACCGATGCCGGCG      ACTACGGCGGCGTGCATACA 1620                      1640
AACAGCGGAATCCCGAACAA      AGCCGCTTACAATACGATTA 1660                      1680
CAAAAATCGGCGTGAACAAA      GCGGAGCAGATTTACTATCG 1700                      1720
TGCTCTGACGGTATACCTCA      CTCCGTCATCAACTTTTAAA 1740                      1760
GATGCAAAAGCCGCTTTGAT      TCAATCTGCGCGGGACCTTT 1780                      1800
ACGGCTCTCAAGATGCTGCA      AGGCTAGAAGCTGCCTGGAA 1820                      1840
TGCAGTCGGATTGTAAACAA      GAAAAGAGACCGGAAATCCG 1860                      1880
GTCTCTTTTTTATATCTAAA      AACATTTCACAGTGGCTTCA

1900
CCATGATC
``` to base substitution, deletion, insertion or transposition, said obtained DNA base sequence encoding the same amino acid sequences as those encoded in base numbers 251 to 913 for a region encoding a peptide for extracellular secretion of neutral protease, base numbers 914 to 1813 for the structural gene for the neutral protease, the base numbers 179 to 184 and 203 to 208 which act as RNA polymerase recognition and binding sites called the promoter region, the ribosome binding region having base numbers to 243 and the terminator region having base numbers 1820 to for showing the end of the genetic information.

4. The recombinant DNA as claimed in claim 1 wherein the vector DNA comprises a plasmid which can be retained in bacterial cells.

5. The recombinant DNA as claimed in claim 4 where the plasmid comprises plasmid pUB110, plasmid pBR322, a portion of the plasmid pUB110 which can be retained in Bacillus cells or a portion of the plasmid pBR322 which can be retained in *Escherichia coli* cells.

6. The recombinant DNA as claimed in claim 5 which is pNP150.

7. A method of producing proteins, comprising the steps of: transforming a host bacterium with a recombinant DNA of about 6.4 kilobase pairs comprising:

(a) a vector DNA which can be retained in said host bacterium, and (b) a DNA fragment inserted into said vector DNA comprising a neutral protease gene of *B. amyloliquefaciens*, Strain F, the DNA fragment having a size of about 1.8 kilobase pairs; and culturing said transformed host bacterium to yield said protein.

8. The method of producing proteins as claimed in claim 7 wherein the DNA fragment comprises a DNA base sequence of:

```
           20                        40
GATCTTAACATTTTTCCCCT    ATCATTTTTCCCGTCTTCAT
           60                        80
TTGTCATTTTTTCCAGAAAA    AATCGTCATTCGACTCATGT
          100                       120
CTAATCCAACACGTCTCTCT    CGGCTTATCCCCTGACACCG
          140                       160
CCCGCCGACAGCCCGCATGG    ACGAATCTATCAATTCAGCC
          180                       200
GCGGAGTCTAGTTTTATATT    GCAGAATGCGAGATTGCTGG
          220                       240
TTTATTATAACAATATAAGT    TTTCATTATTTTCAAAAAGG
          260                       280
GGGATTTATTGTGGGTTTAG    GTAAGAAATTGTCTAGTGCT
          300                       320
GTAGCCGCTTCCTTTATGAG    TTTAACCATCAGTCTGCCGG
          340                       360
GTGTTCAGGCCGCTGAGAAT    CCTCAGCTTAAAGAAAACCT
          380                       400
GACGAATTTTGTACCGAAGC    ATTCTTTGGTGCAATCAGAA
          420                       440
TTGCCTTCTGTCAGTGACAA    AGCTATCAAGCAATACTTGA
          460                       480
AACAAAACGGCAAAGTCCTT    AAAGGCAATCCTTCTGAAAG
          500                       520
ATTGAAGCTGATTGACCAAA    CGACCGATGATCTCGGCTAC
          540                       560
AAGCACTTCCGTTATGTGCC    TGTCGTAAACGGTGTGCCTG
          580                       600
TGAAAGACTCTCAAGTCATT    ATTCACGTCGATAAATCCAA
          620                       640
CAACGTCTATGCGATTAACG    GTGAATTAAACAACGATGTT
          660                       680
TCCGCCAAAACGGCAAACAG    CAAAAAATTATCTGCAAATC
          700                       720
AGGCGCTGGATCATGCTTAT    AAAGCGATCGGCAAATCACC
          740                       760
TGAAGCCGTTTCTAACGGAA    CCGTTGCAAACAAAAACAAA
          780                       800
GCCGAGCTGAAAGCAGCAGC    CACAAAAGACGGCAAATACC
          820                       840
GCCTCGCCTATGATGTAACC    ATCCGCTACATCGAACCGGA
          860                       880
ACCTGCAAACTGGGAAGTAA    CCGTTGATGCGGAAACAGGA
          900                       920
AAAATCCTTGAAAAAGCAAA    ACAAAGTGGGCATGCCGCCA
          940                       960
CAACCGGAACAGGTACGACT    CTTAAAGGAAAAACGGTCTC
          980                      1000
ATTAAATATTTCTTCTGAAA    GCGGCAAATATGTGCTGCGC
         1020                      1040
GATCTTTCTAAACCTACCGG    AACACAAAATAATACGTACG
         1060                      1080
ATCTGCAAAACCGCGAGTAT    AACCTGCCGGGCACACTCGT
         1100                      1120
ATCCAGCACCACAAACCAGT    TTACAACTTCTTCTCAGCGC
         1140                      1160
GCTGCCGTTGATGCGCATAA    CAACCTCGGCAAAGTGTATG
         1180                      1200
AATATTTCTATCAGAAGTAT    AATCGCAACAGCTACGACAA
         1220                      1240
TAAAGGCGGCAAGATCGTAT    CCTCCGTTCAATACGGCAGC
         1260                      1280
AGATACAATAACGCAGCCTG    GATCGGCGACCAAATGATTT
         1300                      1320
ACGGTGACGGCGACGGTTCA    TTCTTCTCACCTCTTTCCGG
         1340                      1360
TTCAATGGACGTAACCGCTC    ATGAAATGACACATGGCGTT
         1380                      1400
ACACAGGAAACAGCCAACCT    GAACTACGAAAATCAGCCGG
         1420                      1440
GCGCTTTAAATGAATCATTC    TCTGATGTATTCGGGTACTT
         1460                      1480
CAACGATACTGAGGACTGGG    ATATCGGTGAAGATATTACG
         1500                      1520
GTCAGCCAGCCGGCTCTCCG    CAGCTTATCCAATCCGACAA
         1540                      1560
AATACGGACAGCCTGATAAT    TTCAAAAATTACAAAAACCT
         1580                      1600
TCCGAACACCGATGCCGGCG    ACTACGGCGGCGTGCATACA
         1620                      1640
AACAGCGGAATCCCGAACAA    AGCCGCTTACAATACGATTA
         1660                      1680
CAAAAATCGGCGTGAACAAA    GCGGAGCAGATTTACTATCG
         1700                      1720
TGCTCTGACGGTATACCTCA    CTCCGTCATCAACTTTTAAA
         1740                      1760
GATGCAAAAGCCGCTTTGAT    TCAATCTGCGCGGGACCTTT
         1780                      1800
ACGGCTCTCAAGATGCTGCA    AGGCTAGAAGCTGCCTGGAA
         1820                      1840
TGCAGTCGGATTGTAAACAA    GAAAAGAGACCGGAAATCCG
         1860                      1880
GTCTCTTTTTTATATCTAAA    AACATTTCACAGTGGCTTCA
         1900
CCATGATC.
```

9. The method of producing proteins as claimed in claim 7 wherein the neutral protease gene comprises a DNA base sequence obtained by subjecting the DNA base sequence of:

```
           20                    40
GATCTTAACATTTTTCCCCT   ATCATTTTTCCCGTCTTCAT
           60                    80
TTGTCATTTTTTCCAGAAAA   AATCGTCATTCGACTCATGT
          100                   120
CTAATCCAACACGTCTCTCT   CGGCTTATCCCCTGACACCG
          140                   160
CCCGCCGACAGCCCGCATGG   ACGAATCTATCAATTCAGCC
          180                   200
GCGGAGTCTAGTTTTATATT   GCAGAATGCGAGATTGCTGG
          220                   240
TTTATTATAACAATATAAGT   TTTCATTATTTTCAAAAAGG
          260                   280
GGGATTTATTGTGGGTTTAG   GTAAGAAATTGTCTAGTGCT
          300                   320
GTAGCCGCTTCCTTTATGAG   TTTAACCATCAGTCTGCCGG
          340                   360
GTGTTCAGGCCGCTGAGAAT   CCTCAGCTTAAAGAAAACCT
          380                   400
GACGAATTTTGTACCGAAGC   ATTCTTTGGTGCAATCAGAA
          420                   440
TTGCCTTCTGTCAGTGACAA   AGCTATCAAGCAATACTTGA
          460                   480
AACAAAACGGCAAAGTCCTT   AAAGGCAATCCTTCTGAAAG
          500                   520
ATTGAAGCTGATTGACCAAA   CGACCGATGATCTCGGCTAC
          540                   560
AAGCACTTCCGTTATGTGCC   TGTCGTAAACGGTGTGCCTG
          580                   600
TGAAAGACTCTCAAGTCATT   ATTCACGTCGATAAATCCAA
          620                   640
CAACGTCTATGCGATTAACG   GTGAATTAAACAACGATGTT
          660                   680
TCCGCCAAAACGGCAAACAG   CAAAAAATTATCTGCAAATC
          700                   720
AGGCGCTGGATCATGCTTAT   AAAGCGATCGGCAAATCACC
          740                   760
TGAAGCCGTTTCTAACGGAA   CCGTTGCAAACAAAAACAAA
          780                   800
GCCGAGCTGAAAGCAGCAGC   CACAAAAGACGGCAAATACC
          820                   840
GCCTCGCCTATGATGTAACC   ATCCGCTACATCGAACCGGA
          860                   880
ACCTGCAAACTGGGAAGTAA   CCGTTGATGCGGAAACAGGA
          900                   920
AAAATCCTTGAAAAAGCAAA   ACAAAGTGGGCATGCCGCCA
          940                   960
CAACCGGAACAGGTACGACT   CTTAAAGGAAAAACGGTCTC
          980                  1000
ATTAAATATTTCTTCTGAAA   GCGGCAAATATGTGCTGCGC
         1020                  1040
GATCTTTCTAAACCTACCGG   AACACAAAATAATACGTACG
         1060                  1080
ATCTGCAAAACCGCGAGTAT   AACCTGCCGGGCACACTCGT
         1100                  1120
ATCCAGCACCACAAACCAGT   TTACAACTTCTTCTCAGCGC
         1140                  1160
GCTGCCGTTGATGCGCATAA   CAACCTCGGCAAAGTGTATG
         1180                  1200
AATATTTCTATCAGAAGTAT   AATCGCAACAGCTACGACAA
         1220                  1240
TAAAGGCGGCAAGATCGTAT   CCTCCGTTCAATACGGCAGC
         1260                  1280
AGATACAATAACGCAGCCTG   GATCGGCGACCAAATGATTT
         1300                  1320
ACGGTGACGGCGACGGTTCA   TTCTTCTCACCTCTTTCCGG
         1340                  1360
TTCAATGGACGTAACCGCTC   ATGAAATGACACATGGCGTT
         1380                  1400
ACACAGGAAACAGCCAACCT   GAACTACGAAAATCAGCCGG
         1420                  1440
GCGCTTTAAATGAATCATTC   TCTGATGTATTCGGGTACTT
         1460                  1480
CAACGATACTGAGGACTGGG   ATATCGGTGAAGATATTACG
         1500                  1520
GTCAGCCAGCCGGCTCTCCG   CAGCTTATCCAATCCGACAA
         1540                  1560
AATACGGACAGCCTGATAAT   TTCAAAAATTACAAAAACCT
         1580                  1600
TCCGAACACCGATGCCGGCG   ACTACGGCGGCGTGCATACA
         1620                  1640
AACAGCGGAATCCCGAACAA   AGCCGCTTACAATACGATTA
         1660                  1680
CAAAAATCGGCGTGAACAAA   GCGGAGCAGATTTACTATCG
         1700                  1720
TGCTCTGACGGTATACCTCA   CTCCGTCATCAACTTTTAAA
         1740                  1760
GATGCAAAAGCCGCTTTGAT   TCAATCTGCGCGGGACCTTT
         1780                  1800
ACGGCTCTCAAGATGCTGCA   AGGCTAGAAGCTGCCTGGAA
         1820                  1840
TGCAGTCGGATTGTAAACAA   GAAAAGAGACCGGAAATCCG
         1860                  1880
GTCTCTTTTTTATATCTAAA   AACATTTCACAGTGGCTTCA
         1900
CCATGATC
``` to base substitution, deletion, insertion or transposition, said obtained DNA base sequence encoding the same amino acid sequences as those encoded in base numbers 251 to 913 for region encoding a peptide for extracellular secretion of neutral protease, base numbers 914 to 1813 for the structural gene for the neutral protease, the base numbers 179 to 184 and 203 to 208 which act as RNA polymerase recognition and binding sites called the promoter region, the ribosome binding region having base numbers to 243 and the terminator region having base numbers 1820 to for showing the end of the genetic information.

10. The method of producing proteins as claimed in claim 7 wherein the vector DNA comprises a plasmid which can be retained in bacterial cells.

11. The method of producing proteins as claimed in claim 10 wherein the plasmid comprises plasmid pUB110, plasmid pBR322, a portion of the plasmid pUBl10 which can be retained in Bacillus cells or a portion of the plasmid pBR322 which can be retained in *Escherichia coli* cells.

12. The method of producing proteins as claimed in claim 11 wherein the recombinant DNA is pNP150 and the host bacterium is a bacterium of the genus Bacillus.

13. A method of producing proteins as claimed in any one of claims 7, 8, 9 and 10 wherein the host bacterium is a bacterium of the genus Bacillus.

* * * * *

UNITED STATES PATENT AND TRADEMARK OFFICE
CERTIFICATE OF CORRECTION

PATENT NO. : 5,612,192
DATED : Mar. 18, 1997
INVENTOR(S) : Furutani et al.

It is certified that error appears in the above-indentified patent and that said Letters Patent is hereby corrected as shown below:

On the title page, item [73], delete "Assignees" and insert
--Assignee--; delete "both".

Signed and Sealed this

Twenty-second Day of July, 1997

Attest:

BRUCE LEHMAN

Attesting Officer      Commissioner of Patents and Trademarks